US011135174B2

(12) United States Patent
Ducheyne et al.

(10) Patent No.: US 11,135,174 B2
(45) Date of Patent: Oct. 5, 2021

(54) COATED MESOPOROUS NANOPARTICLES (75) Inventors: Paul Ducheyne, Rosemont, PA (US);
Sanjib Bhattacharyya, Drexel Hill, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 529 days.

(21) Appl. No.: 14/110,839

(22) PCT Filed: Apr. 12, 2012

(86) PCT No.: PCT/US2012/033250
§ 371 (c)(1),
(2), (4) Date: Jan. 9, 2014

(87) PCT Pub. No.: WO2012/142240
PCT Pub. Date: Oct. 18, 2012

(65) Prior Publication Data
US 2014/0314855 A1  Oct. 23, 2014

Related U.S. Application Data (60) Provisional application No. 61/475,100, filed on Apr. 13, 2011.

(51) Int. Cl.
*A61K 9/51* (2006.01)
*A61K 47/60* (2017.01)
*A61K 9/50* (2006.01)
*A61K 47/69* (2017.01)

(52) U.S. Cl.
CPC .......... *A61K 9/5031* (2013.01); *A61K 9/5089* (2013.01); *A61K 9/5115* (2013.01); *A61K 9/5146* (2013.01); *A61K 9/5192* (2013.01); *A61K 47/60* (2017.08); *A61K 47/6923* (2017.08); *A61K 47/6929* (2017.08)

(58) Field of Classification Search
None
See application file for complete search history.

(56) References Cited

U.S. PATENT DOCUMENTS

| 5,891,548 A | 4/1999 | Graiver et al. | |
| 2006/0018966 A1* | 1/2006 | Lin | A61K 9/143 424/484 |
| 2010/0055000 A1* | 3/2010 | Wei | B01J 20/223 422/400 |
| 2010/0260677 A1* | 10/2010 | Bhatia | A61K 41/0052 424/9.1 |

FOREIGN PATENT DOCUMENTS

| WO | WO 91/011390 | 8/1991 | |
| WO | WO-2010090596 A1 * | 8/2010 | B82Y 30/00 |
| WO | WO 2012/142240 | 10/2012 | |

OTHER PUBLICATIONS

Shen, Hongyan et al.; "Poly(ethylene glycol) Carbodiimide Coupling Reagents for the Biological and Chemical Functionalization of Water-Soluble Nanoparticles," 2009; American Chemical Society, ACS Nano, vol. 4, pp. 915-923.*
Liu, Rui et al.; "Multiresponsive Supramolecular Nanogated Ensembles," 2009; American Chemical Society, JACS vol. 131, p. 15128-15129.*
Groen, Johan C. et al.; "Pore size determination in modified micro- and mesoporous materials. Pitfalls and limitations in gas adsorption data analysis," 2003, Elsevier, Microporous and Mesoporous Materials, vol. 60, pp. 1-17.*
Slowing, Igor et al.; "Mesoporous silica nanoparticles as controlled release drug delivery and gene transfection carriers," 2008, Elsevier; Advanced Drug Delivery Reviews, vol. 60, pp. 1278-1288.*
Bein, Thomas et al.; "Impact of different PEGylation patterns on the long-term bio-stability of Colloidal mesoporous silica nanoparticles," 2010, The Royal Society of Chemistry, Journal of Materials Chemistry, vol. 20, pp. 8693-8699.*
Fuertes, Antonio B. et al.; "Synthesis of Colloidal silica nanoparticles of a tunable mesopore size and their application to the adsorption of biomolecules," 2010, Elsevier, Journal of Colloid and Interface Science, vol. 349, pp. 173-180.*
Fang, Chen et al.; "Functionalized Nanoparticles with Long-Term Stability in Biological Media," 2009, Small, vol. 5, No. 14, pp. 1637-1641 (pp. 1-11, as provided).*
Bein; "Impact of different pegylation patterns on the long-term bio-stability of Colloidal mesoporous silica nanoparticles," 2010, The Royal Society of Chemistry, Journal of Materials Chemistry, vol. 20, pp. 8693-8699.*
Fuertes; "Synthesis of Colloidal silica nanoparticles of a tunable mesopore size and their application to the adsorption of biomolecules," 2010, Elsevier, Journal of Colloid and Interface Science, vol. 349, pp. 173-180.*
Fang; "Functionalized Nanoparticles with Long-Term Stability in Biological Media," 2009, Small, vol. 5, No. 14, pp. 1637-1641.*
Schiestel et al.; "Controled Surface Functionalization of Silica Nanospheres by Covalent Conjugation Reactions and Preparation of High Density Streptavidin Nanoparticles," 2004; ASP, Journal of Nanoscience and Nanotechnology, vol. 4, No. 5, pp. 504-511.*
An et al.; Preparation and self-assembly of carboxylic acid-functionalized silica, 2007; Elsevier; Journal of Colloid and Interface Sciences, vol. 311, pp. 507-513.*
Sun et al.; "Functionalization and bioactivity in vitro of mesoporous bioactive glass," 2008; Elsevier; Journal of Non-Crystalline Solids, vol. 354, pp. 3799-3805.*

(Continued)

*Primary Examiner* — Tigabu Kassa
*Assistant Examiner* — Ivan A Greene
(74) *Attorney, Agent, or Firm* — BakerHostetler (57) ABSTRACT Provided are methods for producing mesoporous nanoparticles that can, once loaded, retain small or large molecules (e.g., molecules having a molecular weight that is less or greater than about 900 Da) until release is desired, upon which time the mesoporous nanoparticles can release the loaded molecule in a controlled manner for a desired period of time, including an extended period of time. Also disclosed are methods for treating a subject comprising administering to the subject a mesoporous nanoparticle according to the present disclosure.

8 Claims, 5 Drawing Sheets

(56) References Cited

OTHER PUBLICATIONS

An et al.; Preparation and self-assembly of carboxylic acid-functionalized silica, 2007; Elsevier; Journal of Colloid and Interface Sciences, vol. 311, pp. 507-513. (Year: 2007).*
Fang; "Functionalized Nanoparticles with Long-Term Stability in Biological Media," 2009, Small, vol. 5, No. 14, pp. 1637-1641 (pp. 1-11, as provided. (Year: 2009).*
Yang et al.; "Hollow Silica Nanocontainers as Drug Delivery Vehicles," 2008; ACS; Langmuir, vol. 24, N, 7, pp. 3417-3421. (Year: 2008).*
Fuertes; "Synthesis of Colloidal silica nanoparticles of a tunable mesopore size and their application to the adsorption of biomolecules," 2010, Elsevier, Journal of Colloid and Interface Science, vol. 349, pp. 173-180. (Year: 2010).*
Levy; "Antimicrobial proteins and peptides: anti infective molecules of mammalian leukocytes," 2004, Journal of Leukocyte Biology, vol. 26, pp. 909-925. (Year: 2004).*
Beck et al.; "Covalent Surface Functionalization and Self-Organization of Silica Nanoparticles," 1999; Wiley-VCH; Angewandte Chemie International Edition vol. 38, No. 9, pp. 1297-1300. (Year: 1999).*
Shen et al.; "Poly(ethylene glycol) Carbodiimide Coupling Reagents for the Biological and Chemical Functionalization of Water-Soluble Nanoparticles," 2009; American Chemical Society; ACS Nano, vol. 3, No. 4, pp. 915-992. (Year: 2009).*
Fisichella et al.; "Uptake of Functionalized Mesoporous Silica Nanoparticles by Human Cancer Cells," 2010, American Scientific Publishers; Journal of Nanoscience and Nanotechnology, vol. 10, pp. 2314-2324. (Year: 2010).*
Cornell, "Newest Factors in Fracture Healing", Clinical Orthopaedics & Related Research, Apr. 1992, 277, 297-311.
Damien et al, "Investigation Of A Hydroxyapatite And Calcium Sulfate Composite Supplemented With An Osteoinductive Factor", J. Biomed. Mater. Res., 1990, 24(6), 639.
Huang et al, Highly Efficient Cellular Labeling Of Mesoporous Nanoparticles In Human Mesenchymal Stem Cells: Implication For Stem Cell Tracking, The FASEB Journal, Dec. 2005, 19, 2014-2016.
Horcajada et al, "Influence of Poor Size of MCM-41 Matrices on Drug Delivery Rate", Microporous Mesoporous Mater., 2004, 68, 105-109.
International Application No. PCT/US12/33250: International Search Report and Written Opinion dated Sep. 12, 2012, 5 pages.
Kawamura et al, "Chondroosteogenetic Response to Crude bone Matrix Proteins Bound to Hydroxyapatite", Clin. Orthop. Relat. Res., 1987, 217, 281-292.
Lelong et al, "Effect of Surfactant Concentration on the Morphology and Texture of MCM-41 Materials", J. Phys. Chem. C, 2008, 112, 10674-10680.
Mal et al, "Photocontrolled Reversible Release Of Guest Molecules From Coumarin-Modified Mesoporous Silica", Nature, Jan. 23, 2003, 421(6921), 350-353.
Pekarek et al, "Double-Walled Microspheres For Drug Delivery", 1993 MRS Fall Meeting, Mater. Res. Soc. Symp. Proc.
Petros et al, "Strategies in the Design of Nanoparticles for Therapeutic Applications", Nature Reviews Drug Discovery, 2010, 9, 615-627.
Radin et al, "Calcium Phosphate Ceramic Coatings As Carriers Of Vancomycin" Jun. 1997, 18(11), 777-782.
Radin et al, "The Controlled Release of Drugs From Emulsified, Sol Gel Processed Silica Microspheres", Biomaterials, 2009, 30, 850-858.
Radin et al, "In Vivo Tissue Response to Resorbable Silica Xerogels as Controlled-Release Materials", Biomaterials, 2005, 26, 1043-1052.
Trewyn et al, "Morphological Control Of Room-Tempature Ionic Liquid Templated Mesoporous Silicia Nanoparticles For Controlled Release Of Antibacterial Agents", Nano Lett., 2004, 4(11), 2139-2143, epublished Sep. 28, 2004.

Uchida, "Calcium Hydroxyapatite Ceramic Delivery-Reply", J. Surg-Brit., 1993, 75, 335.
Cauda et al, "Impact Of Different PEGylation Patterns On The Long-Term Bio-Stability Of Colloidal Mesoporous Silica Nanoparticles", 2010, http://pubs.rsc.orgjenjcontentjarticlepdf/2010jjmjc0jm01390k[retrieved on Aug. 19, 2014].
European Application No. 12771082.0: Extended European Search Report dated Aug. 28, 2014, 13 pages.
Thierry et al, "Electrostatic Self-Assembly Of PEG Copolymers Onto Porous Silica Nanoparticles", Langmuir: The ACS Journal Of Surfaces And Colloids, Aug. 5, 2008, 24(15), 8143-8150.
Arcos et al., "Supramolecular mechanisms in the synthesis of mesoporous magnetic nanospheres for hyperthermia", Journal of Materials Chemistry, 2012, 22, 64-72.
Chen et al., "Preparartion and Release Properties of Sol-Gel Encapsulated Proteins", Journal of Analytical Sciences, Methods and Instrumentation, 2013, 3, 11-16.
Choi et al., "Engineered collagen hydrogels for the sustained release of biomolecules and imaging agents: Promoting the growth of human gingival cells", International Journal of Nanomedicine, 2014, 9, 5189-5201.
Dwivedi et al., "Silica-Coated Liposomes for Insulin Delivery", Journal of Nanomaterials, 2010, 8 pages.
Finnie et al., "Encapsulation and controlled release of biomolecules from silica microparticles", Journal of Materials Chemistry, 2006, 16, 4494-4498.
Gulzar et al., "Stimuli responsive drug delivery application of polymer and silica in biomedicine", Journals of Materials Chemistry B, 2015, 24 pages.
Kecht et al., "Selective Functionalization of the Outer and Inner Surfaces in Mesoporous Silica Nanoparticles", Chem. Mater., 2008, 20, 7207-7214.
Lin et al., "PEG Hydrogels for the Controlled Release of Biomolecules in Regenerative Medicine", Pharmaceutical Research, Mar. 2009, vol. 26, No. 3, 631-643.
Martin-Saavedra et al., "Magnetic mesoporous silica spheres for hyperthermia therapy", Acta Biomaterialia, 2010, 6, 4522-4531.
Molina-Manso et al., "Usefulness of SBA-15 mesoporous ceramics as a delivery system for vancomycin, rifampicin and linezolid: a preliminary report", International Journal of Antimicrobial Agents, 2012, 40, 252-256.
Park et al., "Mesoporous silica as a natural antimicrobial carrier", Colloids and Surfaces A: Physicochemical and Engineering Aspects, 2011, 385, 256-261.
Schwendeman et al., "Injectable controlled release depots for large molecules", Journal of Controlled Release, 2014, 190, 240-253.
Shin et al., "Facile Preparation of Ultra-Large Pore Moseoporous Silica Nanoparticles and Their Application to the Encapsulation of Large Guest Molecules", ACS Appl. Mater Interfaces, 2014, 6, 1740-1746.
Song et al., "The Controlled release of tilmicosin from silica nanoparticles", Drug Development and Industrial Pharmacy, 2011, 37(6), 714-718.
Tang et al., "Poly(lactic acid)-coated mesoporous silica nanosphere for controlled release of venlafaxine", Journal of Colloid and Interface Science, 2011, 360, 488-496.
Vallet-Regi et al., "Evidence of drug confinement into silica mesoporous matrices by STEM spherical aberration corrected microscopy", Chem. Commun., 2010, 46, 2956-2958.
Vathyam et al., "Improving the Adsorption and Release Capacity of Organic-Functionalized Mesoporous Materials to Drug Molecules with Temperature and Synthetic Methods", J. Phys. Chem. C, 2011, 115, 13135-13150.
Verraedt et al., "Controlled release of chlorhexidine from amorphous microporous silica", Journal of Controlled Release, 2010, 142, 47-52.
Shanta Raj Bhattarai et al: "Enhanced Gene and siRNA Delivery by Polycation-Modified Mesoporous Silica Nanoparticles Loaded with Chloroquine", Pharmaceutical Research, Kluwer Academic Publishers-Plenum Publishers, NL, vol. 27, No. 12, Aug. 21, 2010 (Aug. 21, 2010), pp. 2556-2568, XP019862798, ISSN: 1573-904X, DOI: 10.1007/S11095-010-0245-0.

(56) References Cited

OTHER PUBLICATIONS

Yufang Zhu et al: "PEGylated hollow mesoporous silica nanoparticles as potential drug delivery vehicles", Microporous and Mesoporous Materials, Elsevier, Amsterdam, NL, vol. 141, No. 1, Nov. 12, 2010 (Nov. 12, 2010), pp. 199-206, XP028144575, ISSN: 1387-1811, DOI: 10.1016/J.MICROMESO.2010.11.013 [retrieved on Nov. 17, 2010].

* cited by examiner

COATED MESOPOROUS NANOPARTICLES

CROSS-REFERENCE TO RELATED APPLICATIONS

This application is the National Stage of International Application No. PCT/US2012/033250, filed Apr. 12, 2012, which claims the benefit of U.S. Provisional Application No. 61/475,100, filed Apr. 13, 2011, the entire disclosures of which are incorporated herein by reference.

TECHNICAL FIELD

The present disclosure concerns mesoporous nanoparticles that may be used for the delivery of a pharmaceutical agent, as well as the preparation mesoporous nanoparticles.

BACKGROUND

The development of biocompatible, controlled release systems for macromolecules has evolved to the point that biologically active factors can be delivered to a targeted site. R. A. Petros, J. M. DeSimone, Strategies in the design of nanoparticles for therapeutic applications. *Nature Reviews Drug Discovery* (2010) 9, 615-627. The slow release of drugs having a large molecular weight, such as proteins (including growth factors) remains a critical issue with most controlled release systems.

Controlled release of therapeutics is often preferred over traditional therapeutic administration, in which the drug is delivered as a bolus, potentially resulting in drug concentrations exceeding the maximum tolerated dose upon initial administration, and having a limited time frame for efficacy as the concentration in the body is depleted. A delivery method that provides nearly constant drug concentration within the therapeutic window would allow more effective treatment of diseases and would minimize the toxicity risks to the body. Additionally, controlled release may reduce the dosage frequency, and offer site-specific delivery of the therapeutics.

In many of the controlled release formulations, immediately upon placement in an in vitro release medium or an in vivo site, an initial large bolus of drug is released before the release reaches a stable profile. This phenomenon is typically referred to as "burst release" which leads to higher initial drug delivery and also reduces the effective lifetime of therapeutics.

Ceramics and glasses have been widely investigated as materials for the design of artificial bone graft substitutes. In order to further enhance the properties of such materials, bone growth factors and other biologically active molecules have been incorporated for release inside the body and the provision of a beneficial effect on bone tissue healing. K. J. Pekarek, J. S. Jacob and E. Mathiowitz, *Double-walled microspheres for drug delivery. Mater. Res. Soc. Symp. Proc.* (1994) 331, 97-101; Radin S, Campbell J T, Cuckler J M, Ducheyne P. *Calcium-phosphate ceramic coatings as carriers of vancomycin. Biomaterials* 1997; 18:777-82; Cornell C N, Lane J M. *Newest factors in fracture healing. Clin Orthop Rel Res* 1992; 277:297-311; Damien C J, Parsons J R, Benedict J J, Weisman D S. *Investigation of a hydroxyapatite and calcium sulfate composite supplemented with an osteoinductive factor. J Biomed Mater Res* 1990; 24(6):639. Calcium phosphates have been used as carriers for biologically active molecules, but such efforts have met with mixed success. Kawamura M, Iwata H, Sato K, Miura, T., *Chondroosteogenetic response to crude bone matrix proteins bound to hydroxyapatite. Clin Orthop Rel Res* 1987; 217: 281-92; K. J. Pekarek, J. S. Jacob and E. Mathiowitz, *Double-walled microspheres for drug delivery. Mater. Res. Soc. Symp. Proc.* (1994) 331, 97-101. The performance of most of these systems were marred by exhibition of the burst release phenomenon. Uchida A. *Calcium hydroxyapatite ceramic delivery—reply. J Bone J Surg-Brit* 1993; 75: 335.

Silica gel obtained by sol-gel processing is an inorganic polymer produced synthetically by controlled hydrolysis and condensation of alkoxysilanes. This material, originally developed for engineering applications, is currently also studied as a material for both the entrapment and sustained release of bioactive compounds. Important benefits associated with sol-gel processing of biocompatible silica-based glasses are excellent biocompatibility, as demonstrated in vivo (S. Radin, T. Chen, P. Ducheyne, *Emulsified sol-gel silica microspheres for controlled drug delivery, Biomaterials*, in press) and the extensive control of release kinetics (Radin, S., G. El-Bassyouni, E. J. Vresilovic, E. Schepers, and P. Ducheyne, *In vivo tissue response to resorbable silica xerogels as controlled-release materials. Biomaterials*, (2005) 26 1043-52).

In the 1990's, highly ordered mesoporous materials began to attract the attention of the scientific community. Mesoporous materials are characterized by a large specific surface area, a large pore volume, and a particular range of pore sizes (2-50 nm). They also display a narrow pore size distribution. By virtue of these properties, applications for mesoporous materials in the fields of catalysis, lasers, sensors and solar cells have been successfully pursued.

Recent breakthroughs in the synthesis of mesoporous silica materials with high surface areas (for example, greater than 800 m$^2$/g) and tunable pore size (2-10 nm) have led to the development of a series of new delivery systems, where various guest molecules, such as pharmaceutical drugs, fluorescent imaging agents, and other molecules, could be adsorbed into the mesopores and later released into various solutions. See WO 91/011390; Horcajada, P.; Ramila, A.; Perez-Pariente, J.; Vallet-Regi, M. *Influence of pore size of MCM-41 matrices on drug delivery rate. Microporous Mesoporous Mater.* (2004) 68, 105-109; Trewyn, B. G.; Whitman, C. M.; Lin, V. S. Y. *Morphological Control of Room-Temperature Ionic Liquid Templated Mesoporous Silica Nanoparticles for Controlled Release of Antibacterial Agents. Nano Lett.* (2004) 4, 2139-2143. Furthermore, recent reports on the design of functional mesoporous silica materials by decorating the pore surface with organic or inorganic moieties that could serve as gating devices to regulate the release of guest molecules under the control of several different external stimuli, such as chemicals, temperature, redox reactions, and photo-irradiation have highlighted the potential of utilizing this kind of nanodevice for many controlled release applications. It has recently been demonstrated that mesoporous silica nanoparticles can be internalized efficiently into cells, are nontoxic without affecting cell viability, growth, and differentiation, can escape from endo-lysosomal vesicles, and can resist lysosomal degradation. See Mal, N. K.; Fujiwara, M.; Tanaka, Y. *Photocontrolled reversible release of guest molecules from coumarin-modified mesoporous silica. Nature* (London) (2003), 421, 350-353.

However, none of the existing systems involving the use of mesoporous nanoparticles is capable of long-term controlled release of large therapeutic molecules. Furthermore, none are capable of preventing burst release of embedded molecules and then providing desirable release kinetics of large molecules for an extended periods of time. In fact, most current systems are developed for intracellular delivery of therapeutics, concerning which there is no controlled release. New systems for the controlled release of therapeutic agents using mesoporous nanoparticles—themselves known to represent robust, non-toxic agents—would have wide ranging benefits in the drug delivery field.

SUMMARY

In contrast with prior delivery systems using mesoporous nanoparticles, the present disclosure describes the discovery of synthesis conditions that may be used to produce mesoporous nanoparticles that unexpectedly solve the problems of initial burst release and long term delivery of therapeutic moieties. In fact, the present invention pertains to, inter alia, the preparation and use of mesoporous nanoparticles for long-term, zero-order controlled release of therapeutic moieties, without initial burst effect. Previous efforts had also failed to provide mesoporous nanoparticulate systems that can accommodate and deliver larger molecule therapeutic moieties. The present systems are able to deliver large molecules, for example, nucleic acids, proteins, polysaccharides, and other moieties exceeding, for example, 900 Da in size, in a profile characterized by controlled release kinetics over a desired period of time. These discoveries have extremely positive implications for the therapeutic use of mesoporous nanoparticles, which have proven safety, ease of delivery, and hardiness in situ.

Disclosed herein are nanoparticles comprising an inorganic material comprising a plurality of pores of which at least 50% have a diameter of 3.0 to 4.5 nm, and, a coating comprising a biocompatible polymer on the inorganic material, at least some of said pores being loaded with a molecule having a molecular weight that is at least about 900 Da.

Also provided are methods for delivering a pharmaceutical agent to a subject comprising administering to said subject a nanoparticle comprising an inorganic material comprising a plurality of pores of which at least 50% have a diameter of 3.0 to 4.5 nm, and a coating comprising a biocompatible polymer on the inorganic material, at least some of the pores being loaded with the pharmaceutical agent, the pharmaceutical agent having a molecular weight that is at least about 900 Da.

The present disclosure further provides methods for preparing a coated nanoparticle comprising providing a nanoparticle comprising an inorganic material having a plurality of mesopores, increasing the characteristic dimension of at least some of the mesopores, and, coating the nanoparticle with a biocompatible polymer, wherein the nanoparticle has a surface area of less than about 60 m$^2$/g following the coating.

Also disclosed are methods comprising delivering a molecule from a mesoporous nanoparticle at a controlled rate over an extended period of time.

BRIEF DESCRIPTION OF THE DRAWINGS

FIG. 3(a) is a nitrogen gas absorption isotherm of uncoated mesoporous silica nanoparticles, uncoated mesoporous silica nanoparticles that have undergone pore expansion, and PEG-coated mesoporous silica nanoparticles after pore-expansion, while

DETAILED DESCRIPTION OF ILLUSTRATIVE EMBODIMENTS

The present inventions may be understood more readily by reference to the following detailed description taken in connection with the accompanying figures and examples, which form a part of this disclosure. It is to be understood that these inventions are not limited to the specific products, methods, conditions or parameters described and/or shown herein, and that the terminology used herein is for the purpose of describing particular embodiments by way of example only and is not intended to be limiting of the claimed inventions.

In the present disclosure the singular forms "a," "an," and "the" include the plural reference, and reference to a particular numerical value includes at least that particular value, unless the context clearly indicates otherwise. Thus, for example, a reference to "a coating" is a reference to one or more of such coatings and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

Unless otherwise specified, any component, element, attribute, or step that is disclosed with respect to one embodiment of the present methods, products, or systems may apply to any other method, product, or system that is disclosed herein.

The disclosures of each patent, patent application, and publication cited or described in this document are hereby incorporated herein by reference, in their entirety.

Previous attempts to provide controlled release of molecules from mesoporous nanoparticles have been unsuccessful. Existing systems are mostly characterized by slow, incomplete release, or burst release that results in the delivery of most or all incorporated molecules over a shorter than desired period of time. Furthermore, it has not been possible to incorporate larger molecule moieties into mesoporous nanoparticles for subsequent release in situ, despite the utility of many larger molecules (e.g., greater than about 900 Da) for therapeutic applications. The use of large mesopores for accommodating larger molecules has not been successful, as such systems have traditionally exhibited burst-type release, at least because the pores are at least as large as the size of the molecule that is incorporated and the molecule is not well retained.

Thus, the problem of retaining a molecule of a desired size within a mesopore until the proper time for release has traditionally vexed those working in the field. In conventional systems, inorganic mesoporous nanoparticle that are loaded with biological molecules quickly release such molecules shortly after formation. A need has existed for a methods of forming an active agent-loaded mesoporous particle that can be brought to completion before the active agent can escape the pores, i.e., that have sufficient continuity among the various synthesis steps. Beyond the problem of burst release, traditional systems have also suffered from the infirmity of failing to provide controlled release over time.

The present disclosure pertains to systems and methods that solves each of the above-referenced problems, among others. For example, described herein are methods for producing mesoporous nanoparticles that can, once loaded, retain small or large molecules (e.g., molecules having a molecular weight that is less or greater than about 900 Da) until release is desired, upon which time the mesoporous nanoparticles can release the loaded molecule in a controlled manner over a desired period of time. In an exemplary embodiment, a large molecule (trypsin inhibitor, having a molecular weight of 24 kDa) was incorporated within pores of carboxylated mesoporous silica nanoparticles. The loaded mesoporous silica nanoparticles in accordance with the present disclosure are coated with a biodegradable polymer (such as poly(ethylene-glycol)diamine), for example, by covalent bonding, such as by using a crosslinking reagent (for example, 1-ethyl-3-(3-dimethylaminopropyl) carbodiimide (EDAC)). Using the methodologies disclosed herein, it was possible to obtain optimum release kinetics (e.g., zero order release) of the incorporated molecules, without appreciable burst release, with a substantially complete release over a desired, optimum period of time (exceeding, for example, one week).

Disclosed herein are nanoparticles comprising an inorganic material comprising a plurality of pores of which at least 50% have a diameter of 3.0 to 4.5 nm, and, a coating comprising a biocompatible polymer on the inorganic material. In some embodiments, at least some of the pores of the nanoparticles are loaded with a molecule having a molecular weight that is at least about 900 Da. The inorganic material may be, for example, silica, calcium phosphate, hydroxyapatite, alumina, titanium dioxide, or any combination thereof.

The pores of the nanoparticles are sized such that they may be loaded with a desired molecule for eventual release. As used herein, "loading" a pore with a molecule means that the molecule is substantially entirely contained within the void space that is defined by the pore structure. The pores of a given nanoparticle will fall within a certain size distribution. In some embodiments of the present nanoparticles, at least 50%, at least 60%, at least 70%, at least 75%, at least 80%, at least 85%, at least 90%, or at least 95% of the pores have a diameter of 3.0 to 4.5 nm. In other embodiments, at least 50% of the pores of a given nanoparticle have a diameter of about 3 nm, about 3.2 nm, about 3.4 nm, about 3.6 nm, about 3.8 nm, about 4.0 nm, about 4.1 nm, about 4.2 nm, about 4.3 nm, about 4.4 nm, or about 4.5 nm.

The coated nanoparticles may have a surface area of less than about 100 $m^2/g$, less than about 90 $m^2/g$, less than about 80 $m^2/g$, less than about 70 $m^2/g$, less than about 60 $m^2/g$, less than about 50 $m^2/g$, less than about 40 $m^2/g$, less than about 30 $m^2/g$, or less than about 20 $m^2/g$. For example, the surface area of a coated nanoparticle may be about 40 $m^2/g$, about 30 $m^2/g$, or about 20 $m^2/g$.

Any biocompatible polymer, biocompatible copolymer (e.g., alternating, periodic, block, or random, with a linear, branched, star, brush, or comb configuration), or combination of different biocompatible polymers and/or different copolymers may be used for coating the present nanoparticles. The biocompatible polymers that may be used for the coating include synthetic or natural polymers. Natural polymers include, for example, cellulose, collagen, hyaluronic acid, carageenan, alginates, chitosan, gelatin, or any combination thereof. Examples of synthetic biocompatible polymers include ethylene oxide polymers (for example, a polyethylene glycol polymer, such as PEG-bis-amine), polyethyleneimines (PEI), poly(L-lysine) (PLL), poly(aspartic acid) (PAA), polylactides (e.g., PLA, PLLA, PDLLA), polycaprolactones, polydimethylsiloxanes, polyethylenes, polyurethanes, poly(glycolic acid), copolymers of poly(glycolic acid) (such as PGLA, PLAGA, PLGA), copolymers of poly(glycolic acid) and PLA, poly(vinyl) pyrrolidine, or any combination thereof.

One or more crosslinking agents may be used for the coating. The crosslinking agent should be biocompatible. Various crosslinkers are known among those skilled in the art, for example, for specific use in crosslinking polymers of choice, and any such crosslinker(s) may be used. Examples of crosslinkers include but not limited to, Disuccinimidyl glutarate (DSG), Disuccinimidyl suberate (DSS), Dithiobis (succinimidyl propionate) (DSP), Disuccinimidyl tartarate (DST), Ethylene glycol bis(sulfosuccinimidylsuccinate) (Sulfo-EGS), Dimethyl adipimidate.2 HCl (DMA), Dimethyl 3,3'-dithiobispropionimidate.2 HCl (DTBP), Bis(maleimido)ethane (BMOE), 1,4-Bismaleimidyl-2,3-dihydroxybutane (BMDB), 1,6-Hexane-bis-vinylsulfone (HBVS), N-(a-Maleimidoacetoxy) succinimide ester (AMAS), N-[β-Maleimidopropyloxy]succinimide ester (BMPS), Succinimidyl-4-(N-maleimidomethyl)cyclohexane-1-carboxylate (SMCC), N-Succinimidyl 3-(2-pyridyldithio)-propionate (SPDP), Succinimidyl 3-[bromoacetamido]propionate (SBAP), N-Hydroxysuccinimidyl-4-azidosalicylic acid (NHS-ASA), Dicyclohexylcarbodiimide (DCC), 1-Ethyl-3-[3-dimethylaminopropyl]carbodiimide hydrochloride (EDAC), and N-(β-Maleimidopropionic acid) hydrazide, trifluoroacetic acid salt) (BMPH).

In certain embodiments, at least some of the pores of the presently disclosed nanoparticles are loaded with a molecule having a molecular weight that is at least 1 kDa, at least 2 kDa, at least 5 kDa, at least 10 kDa, at least 15 kDa, or at least 20 kDa. Exemplary "large molecules" that may be loaded into the pores of the present nanoparticles include nucleic acids, proteins, DNA, RNA, polysaccharides, carbohydrates, lipids, and other moieties. Any therapeutic or otherwise pharmaceutically active moiety that meets the recited size requirements may be loaded into at least some of the pores of the presently disclosed nanoparticles.

With respect to a given nanoparticle, the loading of the molecule within the pores may be such that the molecule accounts for about 1 wt %, about 3 wt %, about 5 wt %, about 7 wt %, about 10 wt %, about 12 wt %, about 15 wt %, about 16 wt %, about 18 wt %, about 20 wt %, about 22 wt %, about 25 wt %, or about 30 wt %.

Also provided are methods for delivering a pharmaceutical agent to a subject comprising administering to said subject a nanoparticle comprising an inorganic material comprising a plurality of pores of which at least 50% have a diameter of 3.0 to 4.5 nm, and a coating on the inorganic material comprising a biocompatible polymer, at least some of the pores being loaded with the pharmaceutical agent, the pharmaceutical agent having a molecular weight that is at least about 900 Da. The nanoparticles according to the present methods may have any of the characteristics recited above with respect to the inventive nanoparticles. Likewise, the pharmaceutical agent having a molecular weight that is at least about 900 Da may have any of the characteristics recited above with respect to the inventive nanoparticles.

The nanoparticles of the present disclosure may be administered in any desired manner, such as orally or parenterally, neat or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavors, or printing ink. Of course, any material used in preparing any dosage unit form is preferably pharmaceutically pure and substantially non-toxic in the amounts employed. In addition, the nanoparticles may be incorporated into sustained-release preparations and formulations. Parenteral administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the nanoparticles. In tablets, the nanoparticles are mixed with a carrier, diluent or excipient having the necessary compression properties in suitable proportions and compacted in the shape and size desired. For oral therapeutic administration, the nanoparticles may be incorporated with the carrier, diluent, or excipient and used in the form of ingestible tablets, buccal tablets, troches, capsules, elixirs, suspensions, syrups, wafers, and the like. The amount of nanoparticles in such therapeutically useful compositions is preferably such that a suitable dosage will be obtained. The therapeutic compositions preferably contain up to about 99% of the active component.

Liquid carriers, diluents, or excipients may be used in preparing solutions, suspensions, emulsions, syrups, elixirs, and the like. The nanoparticles of this invention can be suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the nanoparticles in the required amounts, in the appropriate solvent, with various of the other ingredients enumerated above, as required, followed by filtered sterilization. Generally, dispersions may be prepared by incorporating the nanoparticles into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the nanoparticles, plus any additional desired ingredient from the previously sterile-filtered solution thereof.

The nanoparticles of the invention may be administered in an effective amount by any of the conventional techniques well-established in the medical field. The nanoparticles employed in the methods of the present invention may be administered by any means that results in the contact of the nanoparticles or the molecule that is loaded within the mesopores of the nanoparticles with the molecules' site or sites of action in the body of a patient. The nanoparticles may be administered by any conventional means available.

A pharmaceutical composition containing the nanoparticles may be in unit dosage form, e.g. as tablets, buccal tablets, troches, capsules, elixirs, powders, solutions, suspensions, emulsions, syrups, wafers, granules, suppositories, or the like. In such form, the composition is sub-divided in unit dose containing appropriate quantities of nanoparticles; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. In addition, dosage forms of the present invention can be in the form of capsules wherein nanoparticles and suitable carriers are formed into a tablet or in the form of a plurality of microtablets, particles, granules or non-perils. These microtablets, particles, granules or non-perils are then placed into a capsule or compressed into a capsule, possibly along with a granulation of the another active ingredient.

The dosage of the nanoparticles of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The present disclosure further provides methods for preparing a coated nanoparticle comprising providing a nanoparticle comprising an inorganic material having a plurality of mesopores, increasing the characteristic dimension of at least some of said mesopores, and, coating said nanoparticle with a biocompatible polymer, wherein the nanoparticle has a surface area of less than about 60 $m^2/g$ following the coating.

Those of ordinary skill in the art are familiar with the preparation of mesoporous nanoparticles from inorganic materials. Traditional methods may be used for this purpose.

Any acceptable methodology may be used to increase the characteristic dimension of at least some of the mesopores of the nanoparticle. For example, hydrothermal treatment, which may include preparing a heated, aqueous emulsion of the nanoparticles, may be used for this purpose. The "characteristic dimension" of a pore represents the smallest dimension of the mouth or opening of the pore at the surface of the nanoparticle. Nanoparticle pores may be substantially round, oval shaped, slit shaped, or irregularly shaped, and the characteristic dimension of any such pore is the minimum distance across the opening thereof. For example, the characteristic dimension of a substantially oval shaped pore is the minor axis, and the characteristic dimension of a slit shaped pore is the width of a slit (not the length).

In some instances, at least about 40%, at least about 50%, at least about 60%, at least about 70%, at least about 75%, at least about 80%, at least about 90%, or at least about 95% of the mesopores of the nanoparticles have a characteristic dimension that is about 2.5 nm or less prior to the step of increasing the characteristic dimension.

The characteristic dimension of at least about 40%, at least about 50%, at least about 60%, at least about 70%, at least about 75%, at least about 80%, at least about 90%, or at least about 95% of the mesopores may be increased by at least about 10%, at least about 15%, at least about 20%, at least about 25%, at least about 30%, at least about 40%, or at least about 50% pursuant to the step of increasing the characteristic dimension. For example, at least about 50% of the mesopores of the nanoparticle may be increased by at least about 70%. In more absolute terms, at least 50% of the mesopores may have a characteristic dimension that is greater than about 3.0 nm following the step of increasing the characteristic dimension. In other instances, following the step of increasing the characteristic dimension, at least 50% of the mesopores may have a characteristic dimension that is 3.0 to 4.5 nm, inclusive.

The surfaces of the respective nanoparticles may be functionalized for any of a number of different purposes. Functionalization may occur during the synthesis of the nanoparticles from inorganic materials, just after the synthesis step, following the step of increasing the characteristic dimension of at least some of the mesopores, or after the step of increasing the characteristic dimension. In one embodiment, functionalization occurs during the synthesis of the mesoporous nanoparticles. Functionalization may comprise adding moieties or molecules containing such moieties to the surface of the nanoparticle to assist in the bonding of the biocompatible polymer coating (if desired) to the nanoparticle (for example, by covalent bonding). Exemplary moieties of this variety include carboxyl groups, amine groups, aldehyde groups, or thiol groups. For example, a molecule for carboxylation of the surface of the nanoparticle is 3-(trimethoxysilyl)-propyl succinic anhydride (TESPA). Aminopropyltriethoxysilane (APTES) may be used to add amine groups to the surface of the nanoparticle. Aldehyde groups may be added using 3-(trimethoxysilyl)-propyl aldehyde. Thiol groups may be added using 3-mercaptopropyltrimethoxysiiane (MPTMS).

Those of ordinary skill in the art are familiar with other types of surface functionalization of nanomaterials. Other surface functionalization includes detection moieties (e.g., fluorescent or radiolabels), gating molecules (e.g., proximate to pores, to permit selective entry and exit from the pores), or to change various properties, such as solubility, conductivity, or magnetism. The nanoparticles may be functionalized in any desired fashion pursuant to the present methods.

The step of coating said nanoparticle with a biocompatible polymer may be carried out in accordance with known procedures for coating nanoparticles. The biocompatible polymer may be any polymer or combination of polymers, as disclosed previously with respect to the inventive coated nanoparticles. Crosslinkers may also be used as disclosed previously. Coating may be accomplished, for example, by covalently bonding the polymer to the nanoparticle, by adsorption, by electrostatic coating, or any desired manner. Unique aspects of the coating of the nanoparticle pursuant to the presently disclosed methods include, among other things, the timing of the coating relative to the other synthesis steps and the thickness of the coating.

The surface area of the nanoparticle following coating with the biocompatible polymer represents a scientifically recognized (albeit indirect) measurement of the thickness of the coating. Prior to the coating step and following the increase of the characteristic dimension of at least some of said mesopores, the uncoated nanoparticles may have a surface area of at least about 400 $m^2/g$, at least about 450 $m^2/g$, at least about 500 $m^2/g$, at least about 650 $m^2/g$, at least about 700 $m^2/g$, at least about 750 $m^2/g$, or at least about 800 $m^2/g$. For example, the surface area of an uncoated nanoparticle may be about 400 $m^2/g$, about 450 $m^2/g$, about 500 $m^2/g$, about 600 $m^2/g$, about 700 $m^2/g$, about 750 $m^2/g$, or about 800 $m^2/g$. Following the coating step, the coated nanoparticles may have a surface area of less than about 100 $m^2/g$, less than about 90 $m^2/g$, less than about 80 $m^2/g$, less than about 70 $m^2/g$, less than about 60 $m^2/g$, less than about 50 $m^2/g$, less than about 40 $m^2/g$, less than about 30 $m^2/g$, or less than about 20 $m^2/g$. For example, the surface area of a coated nanoparticle may be about 40 $m^2/g$, about 30 $m^2/g$, or about 20 $m^2/g$.

Prior to the coating of the nanoparticles and following the increase of the characteristic dimension of at least some of said mesopores, the presently disclosed methods for preparing coated nanoparticles may further comprise loading at least some of said mesopores with a molecule having a molecular weight that is greater than about 900 Da. The molecule having a molecular weight that is at least about 900 Da may have any of the characteristics recited above with respect to the inventive nanoparticles. Incorporation or "loading" of a molecule into at least some of the mesopores may be carried out as disclosed in the present examples, infra, or in accordance with other techniques with which the skilled artisan will be familiar. With respect to a given nanoparticle, the loading of the molecule within the pores may be such that the molecule accounts for about 1 wt %, about 3 wt %, about 5 wt %, about 7 wt %, about 10 wt %, about 12 wt %, about 15 wt %, about 16 wt %, about 18 wt %, about 20 wt %, about 22 wt %, about 25 wt %, or about 30 wt %.

Also disclosed are methods comprising delivering a molecule from a mesoporous nanoparticle at a controlled rate over an extended period of time. As disclosed herein, the present inventors have unexpectedly found that the inventive nanoparticles avoid the problem of initial burst release and are in fact capable of providing controlled release of molecule that has been loaded within at least some of the nanoparticle mesopores. For example, the delivery of the molecule may be characterized by substantially zero order release kinetics. The delivery of the molecule at a controlled rate may be for one week, ten days, two weeks, three weeks, four weeks, five weeks, or six weeks. In other embodiments, the delivery of the molecule at a controlled rate may be over a period of at least one week, at least two weeks, at least three weeks, or at least four weeks. The delivery of the molecule over any such period of time may be characterized by substantially zero order release kinetics. The molecule that is delivered pursuant to the present methods may be a "large molecule", for example, having a molecular weight of at least about 900 Da. To this end, the molecule having a molecular weight that is at least about 900 Da may have any of the characteristics recited above with respect to the inventive nanoparticles.

Example 1—Preparation of PEG-Coated Mesoporous Nanoparticles Loaded with 24 kDa Molecule for Controlled Release Materials. Tetraethylorthosilicate (TEOS), cetyl trimethylammoniumbromide ($C_{18}$TAB), trypsin inhibitor (TI: 24 kDa), sodium hydroxide pellets, polyethyleneglycol-bis-amine (PEG-amine, MW: 3 kDa), 1-ethyl-3-(3-dimethyl-aminopropyl)carbodiimide, hydrochloride (EDAC), 3-(triethoxylsilyl) propyl-succinic anhydride (TESPA), dimethylhexadecylamine (DMH), were obtained from Sigma Aldrich (USA) and all the chemicals used without further purification.

Synthesis. Carboxylated mesoporous silica nanoparticles (MSNs) were prepared as follows: 1.00 g Cetyl trimethyl-ammonium bromide (CTAB) was dissolved in 480 ml nan-opure $H_2O$ at 75° C. The solution was made basic (pH~12) by the addition of 3.5 ml of 2.00M sodium hydroxide (NaOH). After reaching the stable pH=12, 5 ml tetraethylorthosilicate (TEOS) and 1 ml of 3-(trimethoxysilyl)-propyl succinic anhydride was added dropwise. The reaction temperature was maintained at 75° C. for 2 hrs to give rise to white precipitates. The mixture was filtered and washed several times with deionized water until the supernatant shows neutral pH (~7). The samples were then dried in vacuum at 80° C. for 2 days.

Pore Expansion. Dried carboxylated MSNs in the amount of 0.8 g were added to an aqueous emulsion of 0.5 g of the dimethylhexadecylamine (DMH) in 30 ml water and stirred for 15 mins. The emulsion was transferred in to a Teflon coated pressure vessel and kept in the oven at 110° C. for 3 days. After the treatment, it was filtered and washed several times with deionized water to remove unreacted DMH and dried at 80° C. for 1 day.

Removal of Surfactant (CTAB and DMH). To remove the surfactant, 0.8 g of pore expanded MSNs were refluxed in 100 ml methanol containing 1 ml of concentrated hydrochloric acid (HCl) for 48 hrs. The samples were washed several times with ethanol and water, and dried in an oven at 80° C. for 2 days. This is the final MSNs that were used for loading of TI and for polymer coating.

Trypsin Inhibitor Loading and Polymer Coating. 40 mg of TI was dissolved in 0.1 M acetic acid in two separate vials. In one vial, 200 mg of pore expanded MSNs was added, and in a second vial, 200 mg MSNs without pore expansion were added, and the mixtures in each respective vial were stirred for 24 hr. The samples were centrifuged and washed several times with water in order to remove acetic acid. Finally, the samples were dried at 37° C. for 3 days.

A thin layer of PEG-bis-amine was covalently attached to the carboxylated surface of TI loaded pore expanded MSNs. Briefly, 15 mg of polymer PEG-bis-amine was dissolved in 5 ml Tris buffer solution at pH 7.4, 100 mg drug loaded MCM-41-COOH was added and 80 mg EDAC was added as crosslinking agent. The mixture was stirred for 1 hr and was centrifuged and washed several times with water to remove unreacted PEG-bis-amine and EDAC. Subsequently, it was dried at 37° C. for 2 days.

Characterization of MSNs and TI Release Study. The structural morphology of as-synthesized and polymer coated MSNs was characterized by transmission electron microscopy (TEM) (Philips-CM20) and X-ray diffraction (XRD) (Philips PW1830). Gas ($N_2$) sorption/BET analysis (Autosorb-1, Quantachrome, Boynton Beach, Fla.) was used to determine the specific surface area and pore size of non expanded and pore expanded MSNs. The presence of carboxyl groups on MSNs and the actual coating with PEG-bis-amine coating were determined by Fourier transform infrared spectroscopy (FTIR) (Niocolet 5DXC).

For the release study, all three samples were assessed in triplicate in TRIS buffer at pH 7. Briefly, 20 mg of the three samples (non-pore-expanded, pore-expanded, and polymer coated) were taken in duplicates, each in 5 ml of TRIS buffer. The samples were incubated at 37° C. The samples were centrifuged at intervals of 1 hr, 2 hr, 3 hr, 6 hr, 9 hr, and 1 day, and the supernatant was taken. From day 2 onwards, supernatant was collected at each 24 hr interval. This was done until there was no more subsequent release of TI. After each interval, the spent TRIS buffer was replaced by fresh buffer. Released TI was quantified using Quantigold protein reagent (bioWorld, USA).

Figure 1:
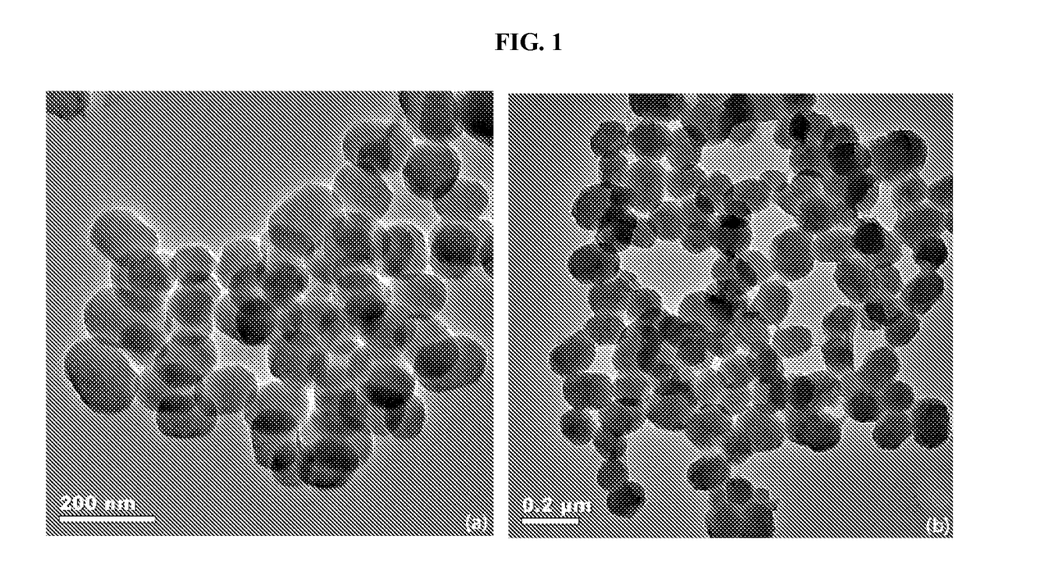
FIG. 1 provides transmission electron microscopy images of (a) as-synthesized mesoporous silica nanoparticles, and (b) pore-expanded polyethylene glycol-coated mesoporous silica nanoparticles.

Results. Transmission electron microscopy images (FIGS. 1(a) and 1(b)) show the spherical morphology of MSNs before and after the polymer coating. The average particle size of the MSNs was 120 nm. It was observed that after polymer coating the particles were more aggregated and more interconnected through a thin layer of PEG, and retain the spherical morphology until the final steps of synthesis process.

Figure 2:
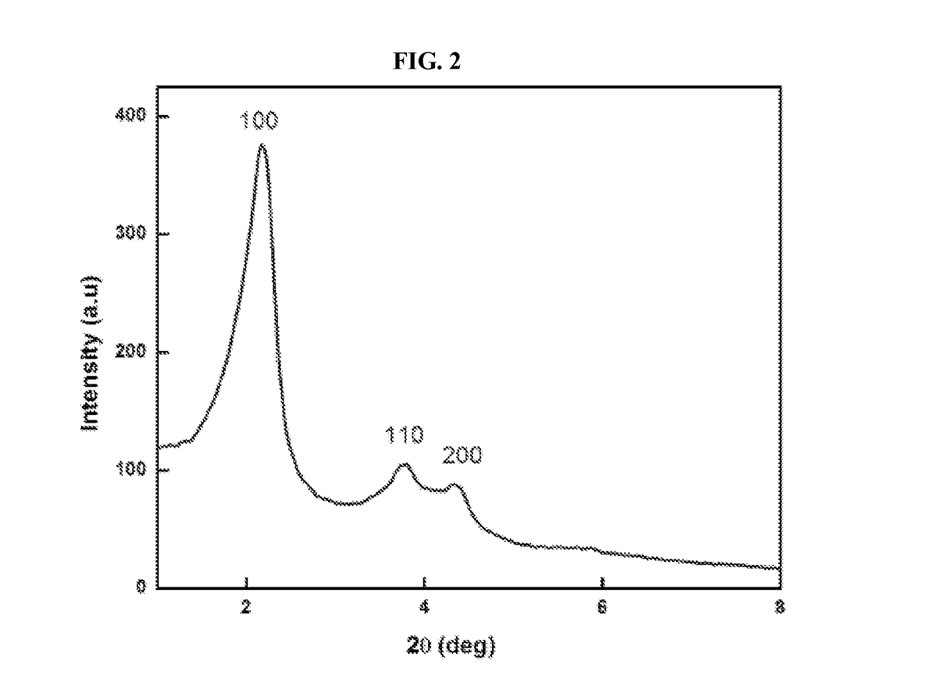
FIG. 2 is an x-ray diffraction pattern of as-synthesized mesoporous silica nanoparticles after surfactant removal.

Powder x-ray diffraction with Cu Kα radiation (λ=0.154 nm) was employed to check the organization of pores within MSNs. FIG. 2 shows the XRD pattern of MSNs after surfactant removal. At low angles, the XRD patterns exhibit three peaks. These peaks correspond to the (100), (110), (200), reticular planes of a hexagonal packing of the pores, and confirmed that the MSNs were MCM-41 type materials (G. Lelong, S. Bhattacharyya, S. Kline, T. Cacciaguerra, M. A. Gonzalez, M. L. Saboungi, *Effect of surfactant concentration on the morphology and texture of MCM-41 materials. J. Phys. Chem. C*, (2008) 112, 10674-10680).

The success story of M41S periodic mesoporous materials is due to their flexibility in terms of synthesis conditions, framework structures and compositions, pore sizes, particle morphology, and texture, and also to their potential use in advanced materials applications. Porous controlled release system for large molecules requires large pore size to incorporate molecules, and can provide controlled release of most of the incorporated molecules. In this case, TI was used as a model molecule for growth factors (e.g., PDGF), which has a minimum molecular dimension of about 3.0 nm. Although it might be possible to squeeze molecules of this size into porous system having average smaller pore size, but release of the molecule will be slow and incomplete. In contrast, the presently disclosed systems provided complete, controlled release.

Figure 3A:
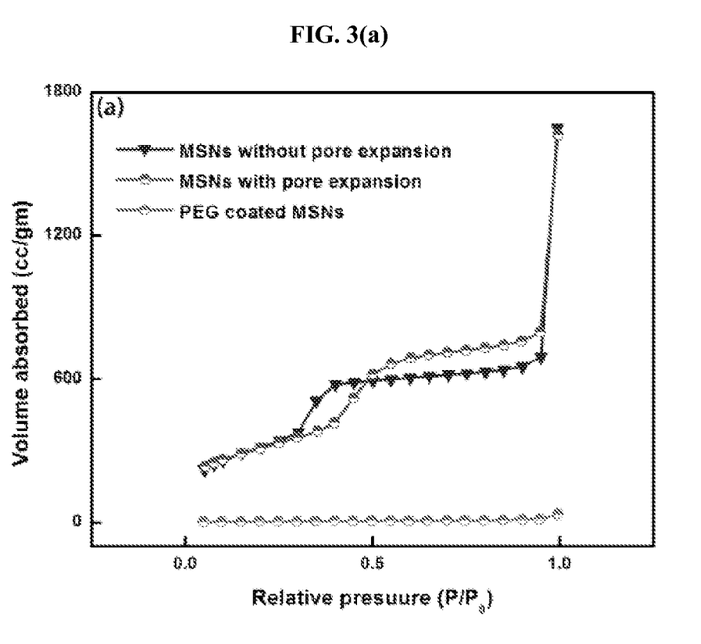
Figure 3B:
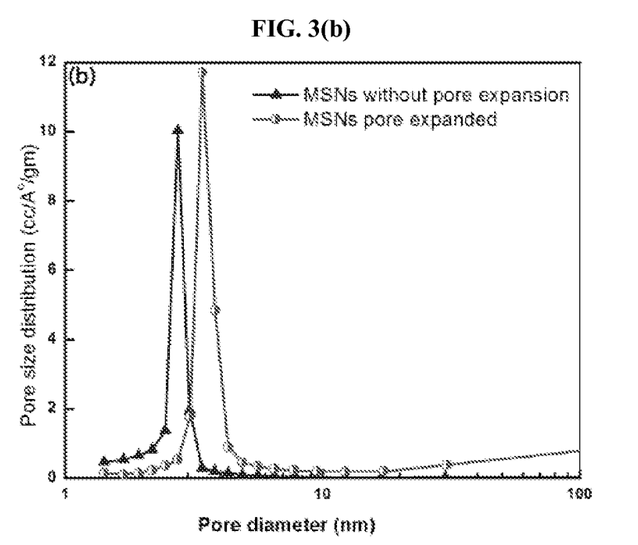
FIG. 3(b) shows the pore size distribution for the mesoporous silica nanoparticles before and after pore expansion.

The most widely used method, nitrogen sorption isotherms, provide the input data for the analysis models for obtaining information regarding pore structure (Dong-Ming Huang, Yann Hung, Bor-Sheng Ko, Szu-Chun Hsu, Wei-Hsuan Chen, Chung-Liang Chien, Chih-Pin Tsai, Chieh-Ti Kuo, Ju-Chiun Kang, Chung-Shi Yang, Chung-Yuan Mou and Yao-Chang Chen., *Highly efficient cellular labeling of mesoporous nanoparticles in human mesenchymal stem cells: implication for stem cell tracking. FASEB. J.*, (2005) 19, 2014-16). FIG. 3(a) shows the type IV isotherm for typical mesoporous silica materials consists of two steps. After the polymer coating isotherm becomes flat like microporous materials which confirm the successful coating. FIG. 3(b) depicts the pore size distribution before and after the pore expansion. Gas sorption analysis (Table 1, below) indicates that as synthesized MSNs have large surface area (~700 $m^2/g$) and pore diameter of 2.5 nm.

TABLE 1

| Sample | BET Surface Area ($m^2$/gm) | Pore Size (nm) | Pore Volume (cc) |
| --- | --- | --- | --- |
| Non-pore expanded MSNs | 697 | 2.7 | 1.63 |
| Pore expanded MSNs | 738 | 3.5 | 1.96 |
| PEG coated, pore-expanded MSNs | 18 | Wide distribution of pore size | |

Hydrothermal treatment resulted in the increase of the surface area of the MSNs (to about 740 $m^2/g$), as well as increased pore diameter (about 3.5 nm). As expected, the polymer coating using the biodegradable polymer PEG drastically reduced the surface area (~18 $m^2/g$) of the MSNs.

Figure 4:
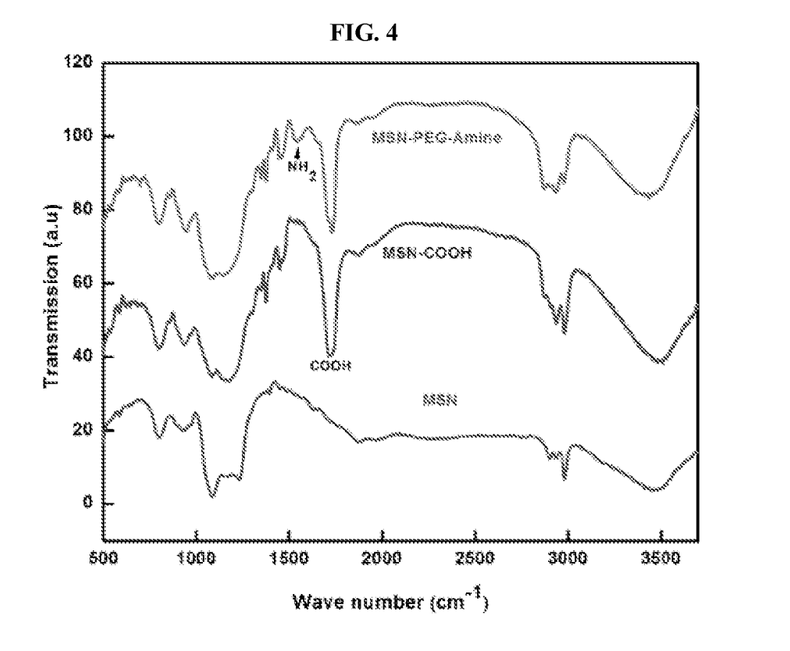
FIG. 4 provides FTIR spectra of as synthesized mesoporous silica nanoparticles, carboxylated mesoporous silica nanoparticles, and PEG coated mesoporous silica nanoparticles.

Before polymer coating, the surface of the MSNs were functionalized with carboxyl groups. FIG. 4 shows the FTIR spectra of carboxylated MSNs and if we compare it the as synthesized MSNs we can see the presence of a new absorption band at 1720 $cm^{-1}$ corresponding to the carboxyl group (range 1700-1800 $cm^{-1}$). This confirms the presence of a carboxyl group on the surface of the MSN, and the absorption band at 1150 $cm^{-1}$ for both carboxylated and non-carboxylated MSNs confirms the intact silica ($SiO_2$) network structure even after functionalization. The presence of the absorption band at 1550 $cm^{-1}$ in the case of PEG-amine coated MSNs, along with all the above mentioned absorption bands, clearly indicates the presence of polymer on the surface of MSNs.

Figure 5A:
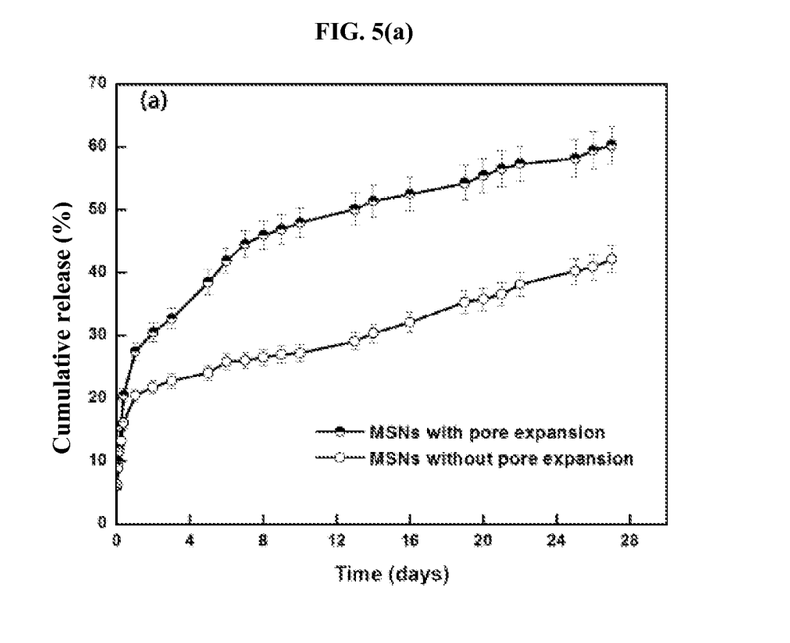
FIG. 5(a) shows the cumulative trypsin inhibitor release from as-synthesized mesoporous silica nanoparticles and pore-expanded mesoporous silica nanoparticles as a function of immersion time up to 4 weeks.

FIG. 5(a) shows the cumulative release for pore expanded and non-expanded MSNs as a function of immersion time up to 28 days (4 weeks). Error bars represent standard deviation (N=3). Data indicate that the release was time-dependent. At the end of the immersion experiment the total cumulative release was 60% for pore-expanded MSNs, and 42% for MSNs with non-expanded pores.

The diffusion-controlled release is that the drug molecules encapsulated in the pores of the silica and liquid penetrates the matrix and dissolves the drug, which then diffuses into the exterior liquid due to concentration gradient. One of the most important controlled release equations is called "Higuchi equation". The Higuchi equation has helped define the mathematical perspective of controlled release drug delivery systems since the era of development of sustained release dosage forms (Gregg, S. J., Sing, K. S. W., (1982), *Adsorption Surface Area and Porosity*; Academic Press: New York). This equation has been applied for diffusion controlled release from a porous matrix, from which a drug is leached by the bathing fluid that penetrates the matrix through pores and capillaries:

$$Q = \sqrt{\frac{D\varepsilon(2A - \varepsilon C)Ct}{\tau}} \quad \text{(Equ. 1)}$$

wherein
Q=amount of drug released after time t;
D=diffusitivity of the drug in the permeating fluid;
τ=the tortuosity factor of the capillary system; the tortuosity indicates that the tortuous path of transport of a drug through porous structure, and accounts for the complexity of pore geometry;

A=the total amount of the drug present in the matrix;
C=the solubility of the drug in the permeating fluid;
ε=the porosity of the matrix. The porosity is the fraction of pores in the system that open to the surface.

The above equation (1) can be expressed in more simple form as:

$$Q = k\sqrt{t} \qquad (\text{Equ. 2})$$

where k is known as Higuchi dissolution constant and treated sometimes in a different manner by different researchers. Thus the cumulative release of drug released is proportional to the square root of time. The above equations are mentioned here only to illustrate the parameters which affect the release from a porous matrix. These equations are not used here to model TI release, since the Higuchi model is valid for the release of relatively small molecules, but not macromolecules.

Figure 5B:
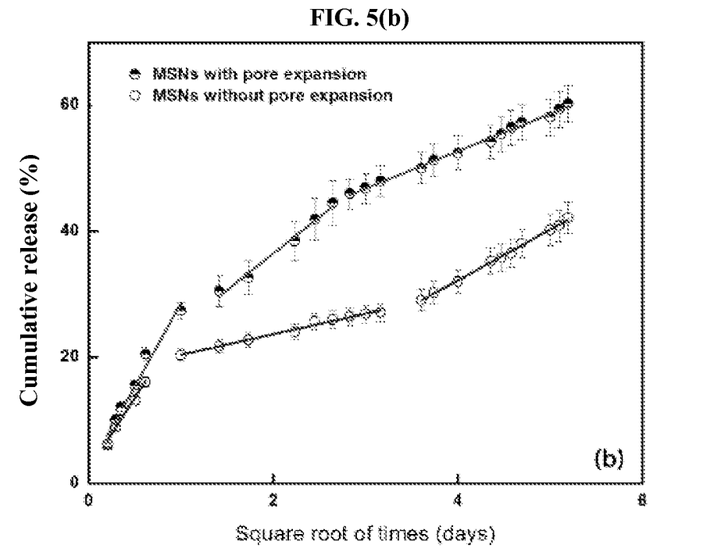
FIG. 5(b) depicts cumulative trypsin inhibitor release as a function of the square root of time, wherein the lines represent linear regression (minimum value of $r^2$ for all of the fittings was 0.96).

FIG. 5(b) shows the same results of FIG. 5(a), but plotted against the square root of time and using linear regression with the origin included among the data. Representation of data in this fashion provides insight as to the possible mechanism of release. The data suggests that there were three stages of release for both samples. In case of pore expanded MSNs there was an initial burst like release for up to day 1. This was followed by two stages of gradual slow release. Both of the latter stages were characterized by a linear relationship against the square root of time. Initial burst-like release is most likely came from the TI absorbed on the surface of MSNs (rather than from within the pores); such surface-absorbed TI became detached from the surface as soon as it is immersed in to the release medium. The gradual slow release in latter stage was likely due to the gradual decrease of the quantity of TI present inside the pores over the total period of release.

In case of MSNs with non-expanded pores, initial burst release was likely due to the same reason observed above for pore-expanded MSNs, but a second stage of very slow release was also observed. As discussed earlier, pores are tightly packed with TI and initially there is very little physical room for ambient medium to enter into the pores and cause outward diffusion of the TI molecules, until after about 10 days of release. After that period a faster release rate was observed, as the access of the release medium to the inside of the pores increased with time. It is noteworthy that all the stages of TI release are linear in nature when plotted against square root of times, indicating the diffusion is the likely rate-controlling mechanism in the conditions of the experiment.

Figure 6A:
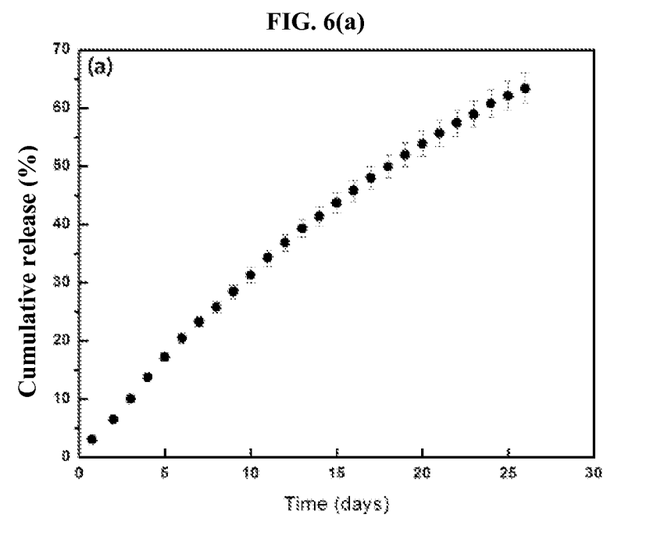
FIG. 6(a) shows cumulative trypsin inhibitor release from PEG coated pore-expanded mesoporous silica nanoparticles as a function of immersion time up to 4 weeks, wherein error bars represent standard deviation (N=3).
Figure 6B:
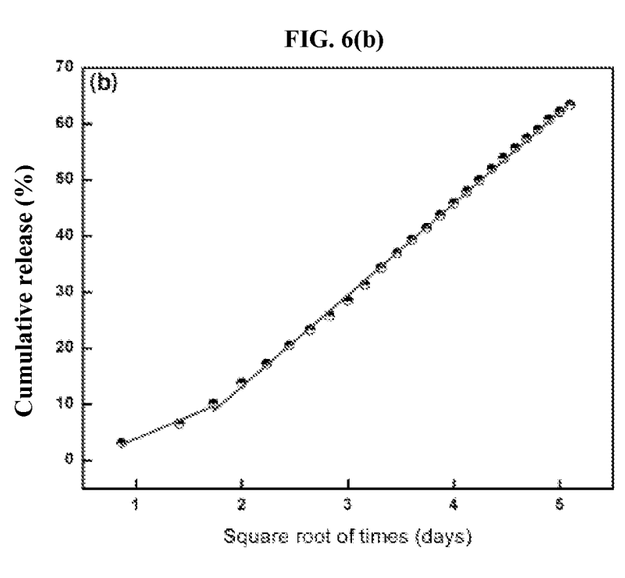
FIG. 6(b) depicts cumulative trypsin inhibitor release as a function of the square root of time, wherein the lines represent linear regression ($r^2$ equal to 0.95 and 0.99).

FIG. 6(a) shows the cumulative release of TI from PEG coated, pore-expanded MSNs. These samples provided an almost zero order release over the entire release period, with a total 65% of the pore-absorbed TI released at the end of 4 weeks. Initial bust release was not observed. FIG. 6(b) shows the same result as in FIG. 6(a), plotted against square root of times. It reveals that the initial period of release is slightly slower than the release rate over the remainder of the period (which was effectively constant).

The polymer coating also prevented burst-type release of TI that was absorbed onto the surface of the MSNs (rather than within the pores). As time passes, however, the polymer layers swell, and ambient medium penetrates the pores of the MSNs, causing slow diffusion of the drugs out of the pores and through the polymer layer. Not wishing to be bound by any particular theory of operation, it may be that the release kinetics is controlled by the rate of diffusion of TI from pores in combination with the rate of degradation of polymer. Possibly due to combined effect of these two phenomena, the MSNs produced herein provided an almost zero order release of TI for an extended period of time. The properties of these materials provide the basis for the controlled release of bioactive molecules under clinically relevant conditions.

What is claimed:

1. A coated, loaded, non-hollow mesoporous silica nanoparticle (MSN) comprising:
    an inorganic material comprising silica and a plurality of pores of which at least 50% have a diameter of 3.0 to 4.5 nm,
    wherein the surfaces of the inorganic material are functionalized with carboxyl moieties;
    wherein at least some of the pores are loaded with a therapeutic molecule having a molecular weight that is at least about 900 Da;
    wherein the loaded MSN-is coated with biodegradable polymer molecules that are covalently bonded in polymeric form to the functionalized surfaces of the inorganic material, thereby providing a coating of the biodegradable polymer molecules, and wherein the coating includes a crosslinking agent;
    wherein loading of at least some of the pores with the therapeutic molecule occurs prior to formation of the coating;
    wherein the MSN has a surface area in the absence of the coating of at least about 500 m$^2$/g,
    wherein the coated, loaded, non-hollow MSN that is loaded with the therapeutic molecule has a surface area of less than about 100 m$^2$/g, and
    wherein, when the MSN is immersed in TRIS buffer at pH 7 and 37° C., the MSN releases the therapeutic molecule with substantially zero order release kinetics with a controlled rate for at least one week via diffusion of the therapeutic molecule from the pores through the coating and via degradation of the coating without an initial burst release.

2. The coated, loaded, non-hollow MSN according to claim 1 wherein at least 90% of said pores have a diameter of 3.0 to 4.5 nm.

3. The coated, loaded, non-hollow MSN according to claim 1 wherein said biodegradable polymer is an ethylene oxide polymer.

4. The coated, loaded, non-hollow MSN according to claim 1 wherein said biodegradable polymer is polyethylene glycol.

5. The coated, loaded, non-hollow MSN according to claim 1, wherein the therapeutic molecule has a molecular weight that is at least about 5 kDa.

6. A method for delivering a therapeutic molecule to a subject comprising: administering to said subject the coated, loaded, non-hollow mesoporous silica nanoparticle of claim 1.

7. The coated, loaded, non-hollow MSN according to claim 1, wherein the MSN releases the therapeutic molecule with zero order release kinetics.

8. The coated, loaded, non-hollow MSN according to claim 1, wherein the therapeutic molecule has a molecular weight that is at least about 5 kDa.

* * * * *

UNITED STATES PATENT AND TRADEMARK OFFICE
CERTIFICATE OF CORRECTION

| | | |
|---|---|---|
| PATENT NO. | : 11,135,174 B2 | |
| APPLICATION NO. | : 14/110839 | |
| DATED | : October 5, 2021 | |
| INVENTOR(S) | : Paul Ducheyne et al. | |

It is certified that error appears in the above-identified patent and that said Letters Patent is hereby corrected as shown below:

In the Claims

Column No. 16, Line no. 57-59, Replace:
"7. The coated, loaded, non-hollow MSN according to
claim 1, wherein the MSN releases the therapeutic molecule with zero order release kinetics."

With:
-- 7. A pharmaceutical composition comprising
a coated, loaded, non-hollow MSN according to claim 1 and a pharmaceutically acceptable carrier, diluent, or excipient. --

Column No. 16, Line no. 60-62, Replace:
"8. The coated, loaded, non-hollow MSN according to
claim 1, wherein the therapeutic molecule has a molecular weight that is at least about 5 kDa."

With:
-- 8. The coated, loaded, non-hollow MSN according to claim 1, wherein the MSN releases the therapeutic molecule with zero order release kinetics. --

Signed and Sealed this
Seventh Day of June, 2022

Katherine Kelly Vidal
*Director of the United States Patent and Trademark Office*